United States Patent [19]

Weerstra

[11] Patent Number: 5,760,297
[45] Date of Patent: Jun. 2, 1998

[54] SYSTEM FOR MEASURING ACID CONCENTRATION IN AN ALKYLATION PROCESS

[75] Inventor: Douglas D. Weerstra, Arvada, Colo.

[73] Assignee: Mesa Laboratories, Inc., Lakewood, Colo.

[21] Appl. No.: 823,087

[22] Filed: Mar. 24, 1997

Related U.S. Application Data

[60] Provisional application No. 60/017,340, Apr. 26, 1996.
[51] Int. Cl.⁶ .................. G01N 9/18; C07C 3/54
[52] U.S. Cl. .............. 73/53.01; 73/54.02; 73/54.41
[58] Field of Search ................. 73/53.01, 54.17, 73/54.41, 54.02; 260/683.59, 683.47, 78 R, 30.8 R, 459 R; 568/785, 790

[56] References Cited

U.S. PATENT DOCUMENTS

| | | | |
|---|---|---|---|
| 2,869,357 | 1/1959 | Kritz | 73/32 |
| 2,990,714 | 7/1961 | Smith | 73/53 |
| 3,513,220 | 5/1970 | Brandel | 260/683.59 |
| 3,653,835 | 4/1972 | Brandel | 23/230 R |
| 3,671,542 | 6/1972 | Kwolek | 260/30.8 R |
| 3,819,587 | 6/1974 | Kwolek | 260/78 R |
| 4,018,846 | 4/1977 | Mayer | 260/683.59 |
| 4,073,822 | 2/1978 | Meyer | 260/683.47 |
| 4,226,796 | 10/1980 | Akred et al. | 260/459 R |
| 5,034,497 | 7/1991 | Waitkus | 528/129 |
| 5,238,598 | 8/1993 | Kurimoto et al. | 252/299.6 |
| 5,365,778 | 11/1994 | Sheen et al. | 73/54.41 |
| 5,387,725 | 2/1995 | Walters et al. | 568/779 |
| 5,433,893 | 7/1995 | Jost et al. | 252/514 |
| 5,554,671 | 9/1996 | Craun et al. | 523/408 |

Primary Examiner—Hezron E. Williams
Assistant Examiner—J. David Wiggins
Attorney, Agent, or Firm—Dorr, Carson, Sloan & Birney, P.C.

[57] ABSTRACT

A system for measuring acid concentration in an alkylation process by repeatedly measuring the density, viscosity or velocity of sound through a sample over time as volatile organic compounds (VOCs) are allowed to escape and the sample stratifies. A partial vacuum can be used to accelerate dissipation of light VOCs from the sample. A processor applies a predetermined function to a series of these sound velocity measurements to compute the acid concentration in the sample. The function can be determined by statistical regression against sound velocity measurements taken from samples having known acid concentrations. The system can be used either to generate a read-out to facilitate manual control of the alkylation process, or to automatically regulate the acid feed rate to maintain a desired acid concentration.

19 Claims, 4 Drawing Sheets

SYSTEM FOR MEASURING ACID CONCENTRATION IN AN ALKYLATION PROCESS

RELATED APPLICATION

The present application is based on the Applicant's U.S. Provisional Patent Application Ser. No. 60/017,340, entitled "System For Measuring Acid Concentration In An Alkylation Process", filed on Apr. 26, 1996.

BACKGROUND OF THE INVENTION

1. Field of the Invention

The present invention relates generally to the field of alkylation processes used primarily in the petroleum refining industry. More specifically, the present invention discloses a system for rapidly and accurately measuring acid concentration to optimize control in an alkylation process.

2. Statement of the Problem

Alkylation processes have long been widely used in the chemical field. In the petroleum refining industry, alkylation is commonly used to convert paraffins and olefins (e.g., isobutane and butene) that are byproducts of other refinery processes into octane and related compounds that are high quality fuels for engines. Highly concentrated sulfuric acid ($H_2SO_4$) or hydrofluoric acid (HF) is used as a catalyst. There are several methods for alkylation that are well known in the petroleum refining art. While only one of these alkylation method is discussed in detail below, the present invention can be used for the measurement of acid concentration in other types of alkylation processes.

As shown in FIG. 1, isobutane, butene, and the acid catalyst are combined in a first contactor vessel 10. Efficient mixing with fine subdivision must be-provided by agitating the mixture. The resulting products are then drawn into a settler 11 where the high octane products are separated and withdrawn from the process. The remaining material is largely acid, but also contains significant amounts of water, paraffins, olefins, sulfonated compounds, and other contaminants. For example, the acid entering the first contactor 10 typically has a concentration of approximately 98 percent, while the acid concentration in the settler 11 is about 96 percent.

In the second stage of the process, acid from the first settler 11 is fed into a second contactor 12, as shown in FIG. 1, and mixed with additional isobutane and butene. The resulting products are drawn into the second settler 13 where the octane is separated and withdrawn. The acid concentration in the second settler 13 is reduced again by about 2 percent to approximately 94 percent.

This sequence of steps is repeated in the third and fourth stages by processing the acid and additional amounts of isobutane and butene through a third contactor 14 and third settler 15, and then through a fourth contactor 16 and fourth settler 17. The acid concentration in the third settler 15 is reduced to approximately 92 percent and the acid concentration in the fourth settler 17 is reduced to approximately 90 percent. The acid leaving the fourth settler 17 is shipped back to the manufacturer for regeneration.

The processing equipment is quickly damaged and the efficiency of the chemical process plunges if the acid concentration drops too low. If it becomes necessary to shut down the alkylation process, isobutane and butene will continue to be produced as byproducts of other petroleum refinery processes. These compounds cannot be readily stored and must be disposed of by flaring. This represents an economic loss to the refiner and can raise environmental concerns. Therefore, the concentration of the acid must be carefully controlled at each stage in the alkylation process to prevent downtime.

It is also important to minimize acid consumption to minimize operating costs. In a conventional plant, the acid leaving the fourth settler 17 is sampled once or twice each day. These samples are sent to a laboratory for analysis, which requires several hours to obtain results. This situation induces an operator to run the plant in a very conservative manner to avoid any possibility that the acid concentration in the alkylation process might fall too low. The conventional approach is to set the feed rate of acid into the first contactor 10 so that acid leaving the fourth settler 17 has a concentration of at least 90 percent. Additional acid can be fed directly into the second, third, and fourth contactors to ensure an adequate acid concentration at each step in the process. This conservative manner of operation causes a substantial increase in operating costs due to the large quantities of acid used by a typical plant over time.

Several prior art patents have been issued in this general field, including the following:

| Inventor | U.S. Pat. No. | Issue Date |
|---|---|---|
| Brandel | 3,513,220 | May 19, 1970 |
| Brandel | 3,653,835 | April 4, 1972 |
| Mayer | 4,018,846 | April 19, 1977 |
| Mayer | 4,073,822 | Feb. 14, 1978 |

The Brandel patents disclose a specific gravity analyzer for controlling an alkylation process. The Brandel system continuously measures the specific gravity of the acid catalyst. Volatile organic compounds (VOCs) are stripped by heating the sample stream and using a differential pumping system. The specific gravity is then measured by a strain gauge 58 that monitors the buoyant force on a "displacemeter" 56 (i.e., a weight) immersed in the sample (column 5, lines 46–55). The Brandel system is designed for continuous operation by maintaining a continuous sample stream through the cavity 52 containing the displacemeter 56. However, nothing in Brandel suggests taking a series of density measurements over time from the same sample as VOCs escape.

The Mayer patents disclose a method of continuously controlling the water content of sulfuric acid used as a catalyst in an alkylation process. The catalyst is contacted with fuming sulfuric acid of known concentration at a sufficient flow rate to maintain the mixture at the point of incipient fuming. A $SO_3$ detector monitors the presence of $SO_3$ and controls the rate of fresh acid makeup by comparing the flowrates of $SO_3$ and the sample acid. This system requires a costly source of $SO_3$ of known concentration and large quantities of sample acid.

3. Solution to the Problem

None of the prior art references uncovered in the search measure acid concentration in an alkylation process by taking a series of sound velocity measurements over time for a single sample as VOCs escape and the sample stratifies. In the preferred embodiment, the velocity of sound through the sample is measured and a partial vacuum is drawn to accelerate dissipation of light VOCs over time. The time series of readings is normalized for temperature. A predetermined function using coefficients determined by statistical regression is then applied to the time series of readings to compute acid concentration. This system allows the acid concentration to be quickly determined with a high degree of accuracy, regardless of sample's VOC contents. A number of these systems can be used to monitor the acid concentration for each stage of the alkylation process to closely regulate the acid feed Fate for optimum efficiency.

SUMMARY OF THE INVENTION

This invention provides a system for measuring acid concentration in an alkylation process by making repeated measurements of the sound velocity through a sample over time as volatile organic compounds (VOCs) are allowed to escape and the sample stratifies. A partial vacuum can be used to accelerate dissipation of VOCs from the sample. A computer or micro processor applies a predetermined function to a series of these sound velocity measurements to compute the acid concentration in the sample. The function can be determined by regression against sound velocity measurements taken from samples having known acid concentrations. The system can be used either to generate a read-out to facilitate manual control of the alkylation process, or to automatically regulate the acid feed rate to maintain a desired acid concentration.

A primary object of the present invention is to provide a system for quickly and accurately determining acid concentration in an alkylation process.

Another object of the present invention is to provide a system for accurately monitoring acid concentration to minimize use of acid in an alkylation process, and thereby reduce operating costs and environmental concerns.

Yet another object of the present invention is to provide a system for accurately controlling operation of an alkylation plant to minimize down time.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
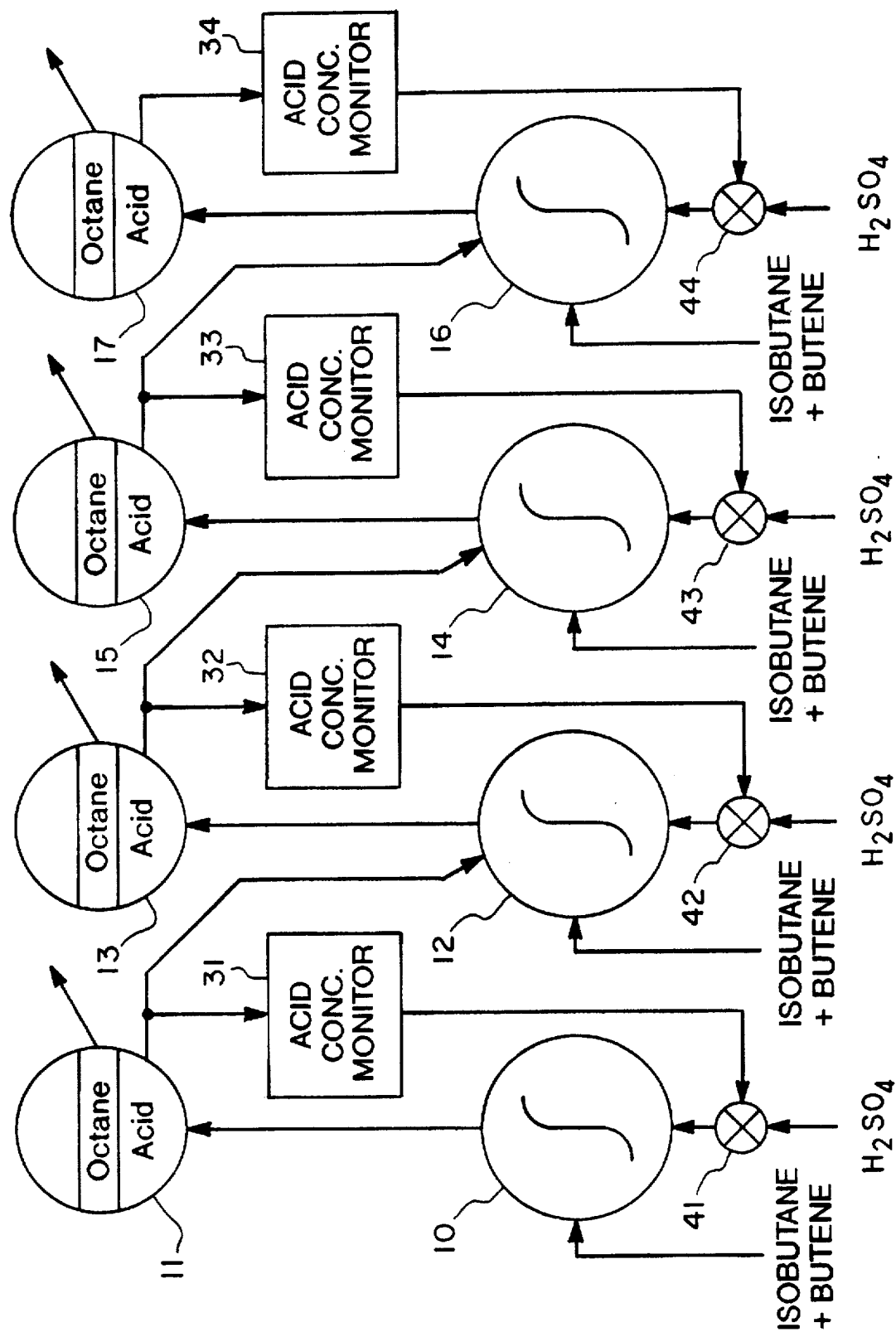
FIG. 1 is a simplified block diagram of an alkylation plant using the present invention to regulate the feed rate of acid into each contactor.

Turning to FIG. 1, a schematic diagram is provided showing a four-stage alkylation plant that has been retrofitted with acid concentration monitoring systems 31, 32, 33, and 34, each embodying the present invention. As previously discussed, isobutane butene, and the acid catalyst are combined in a first contactor 10 and the resulting products are then drawn into a settler 11 where the high octane products are separated and withdrawn from the process. The first monitor 31 measures the acid concentration in the first settler 11.

In the second stage of the process, acid from the first settler 11 is fed into a second contactor 12 and mixed with additional isobutane and butene. The resulting products are drawn into the second settler 13 where the octane is separated and withdrawn. The second monitor 32 measures the acid concentration in the second settler 13. This sequence is repeated in the third and fourth stages by processing the acid and additional amounts of isobutane and butene through a third contactor 14 and third settler 15, and then through a fourth contactor 16 and fourth settler 17. The acid concentration in the third settler 15 is measured by the third monitor 33, and the acid concentration in the fourth settler 17 is measured by the fourth monitor 34.

Figure 2:
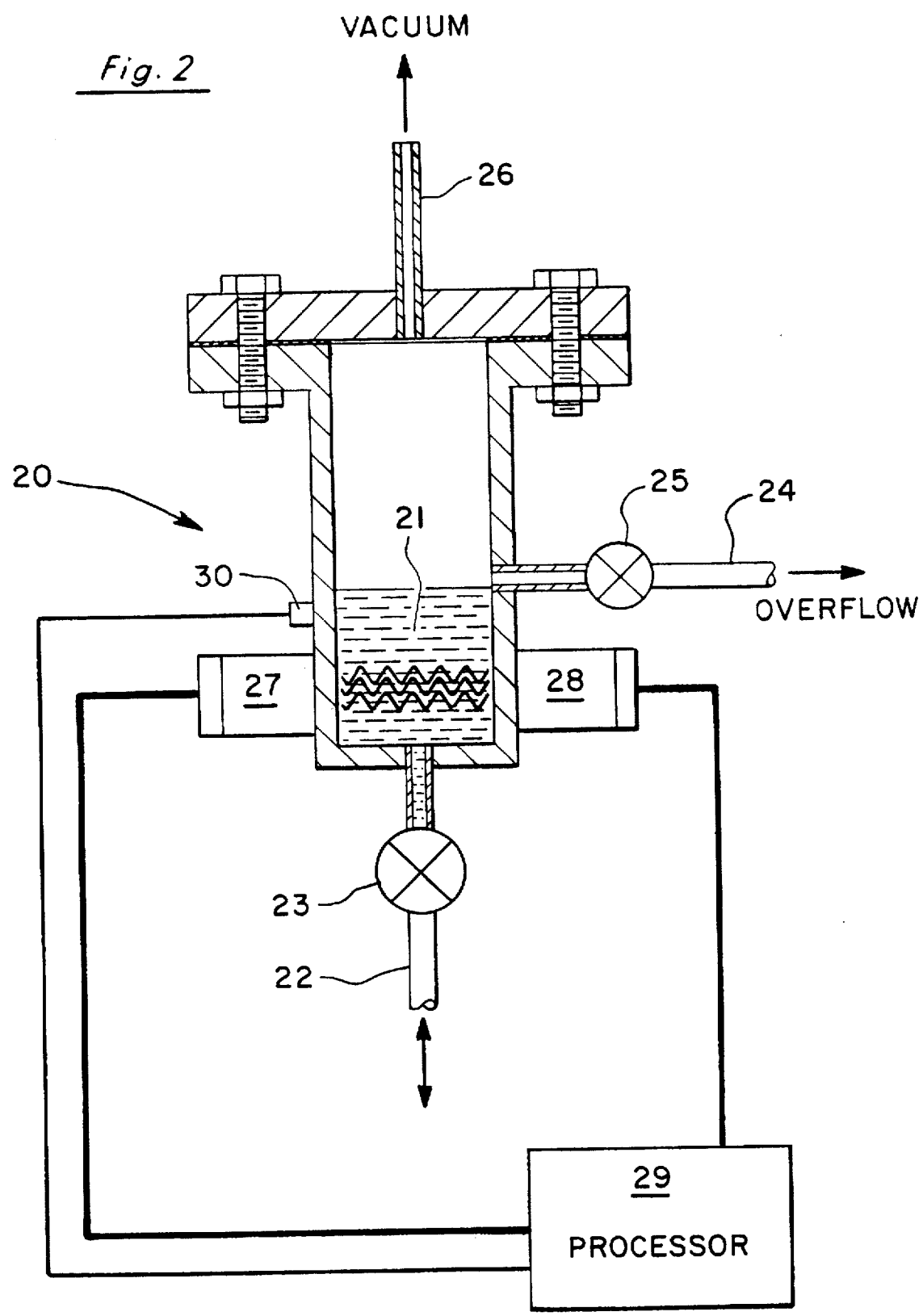
FIG. 2 is a simplified cross-sectional view of the monitor cell 20 used to hold a sample 21 of the acid catalyst.

FIG. 2 illustrates the acid concentration monitor. A monitor cell 20 is used to hold a sample 21 drawn from the acid phase contained in the settler. The sample 21 flows into the cell 20 through an inlet port 22 and inlet valve 23. The maximum fluid level of the sample 21 in the cell 20 is fixed by an overflow port 24. After the cell has been filled, the inlet valve 23 and overflow valve 25 are both closed and a partial vacuum is drawn through the vacuum port 26 for a period of time to accelerate dissipation of the VOCs from the sample 21. After a period of time, the vacuum is removed by venting the cell through vacuum port 26.

Two sonic transducers 27 and 28 located on opposing sides of the lower portion of the cell 20 are used to transmit and receive sonic pulses through the sample. In the preferred embodiment, both are piezoelectric transducers that can be used interchangeably to transmit and receive. An input voltage causes the transmitting transducer to generate a pulse, which is received by the other transducer, which generates an output voltage pulse. The delay between the input voltage and the resulting output voltage pulse is timed to determine the velocity of sound through the sample 21.

A computer processor 29 controls the sonic transducers 27, 28. After the monitor cell 20 has been filled with a sample 21, the processor 29 uses the sonic transducers 27, 28 to repeatedly measure the velocity of sound through the sample 21. In the preferred embodiment, these sound velocity measurements begin shortly after the sample 21 is drawn into the cell 20, continue through the period while the vacuum is on, and then continue for a fixed time thereafter (e.g., 10 to 30 minutes). After the sound velocity measurements have been made, the processor 29 controls the inlet valve 23 and overflow valve 25 to open and thereby allow the sample 21 to drain from the cell 20 through the inlet port 22.

Figure 3:
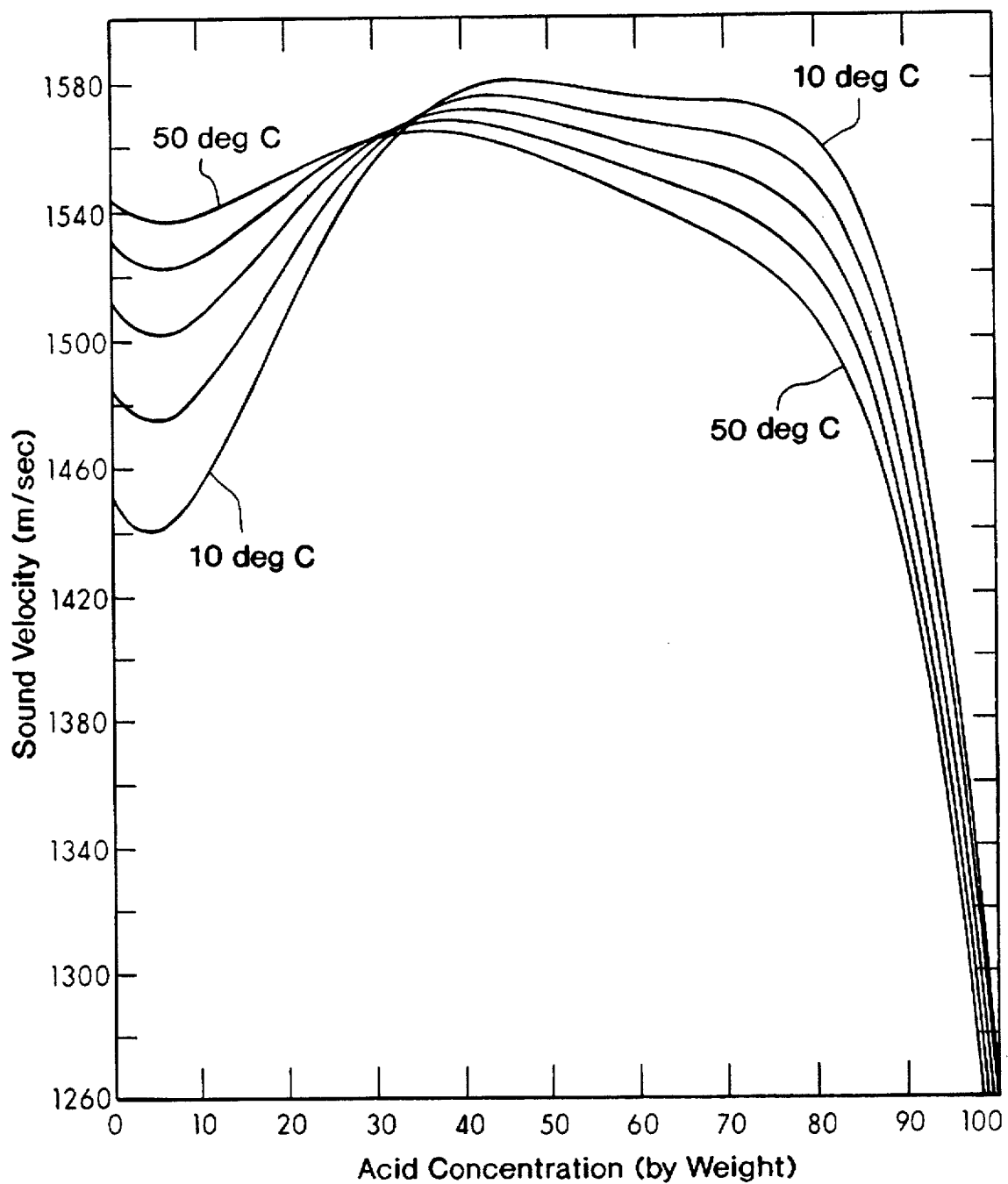
FIG. 3 is a graph showing the velocity of sound in clean sulfuric acid as a function of temperature and concentration.

A temperature sensor 30 (e.g., an RTD) is inserted into the cell 20 to measure the temperature of the sample 21. FIG. 3 is a graph showing the typical velocity of sound in clean sulfuric acid as a function of acid concentration and temperature. Note that the extreme right-hand region of the curves is approximately linear for acid concentrations of 85% to 100%, which greatly simplifies temperature normalization within the range of acid concentrations of interest. The processor 29 is programmed to normalize the sound velocity measurements for variations in the temperature measured by the temperature sensor 30.

Figure 4:
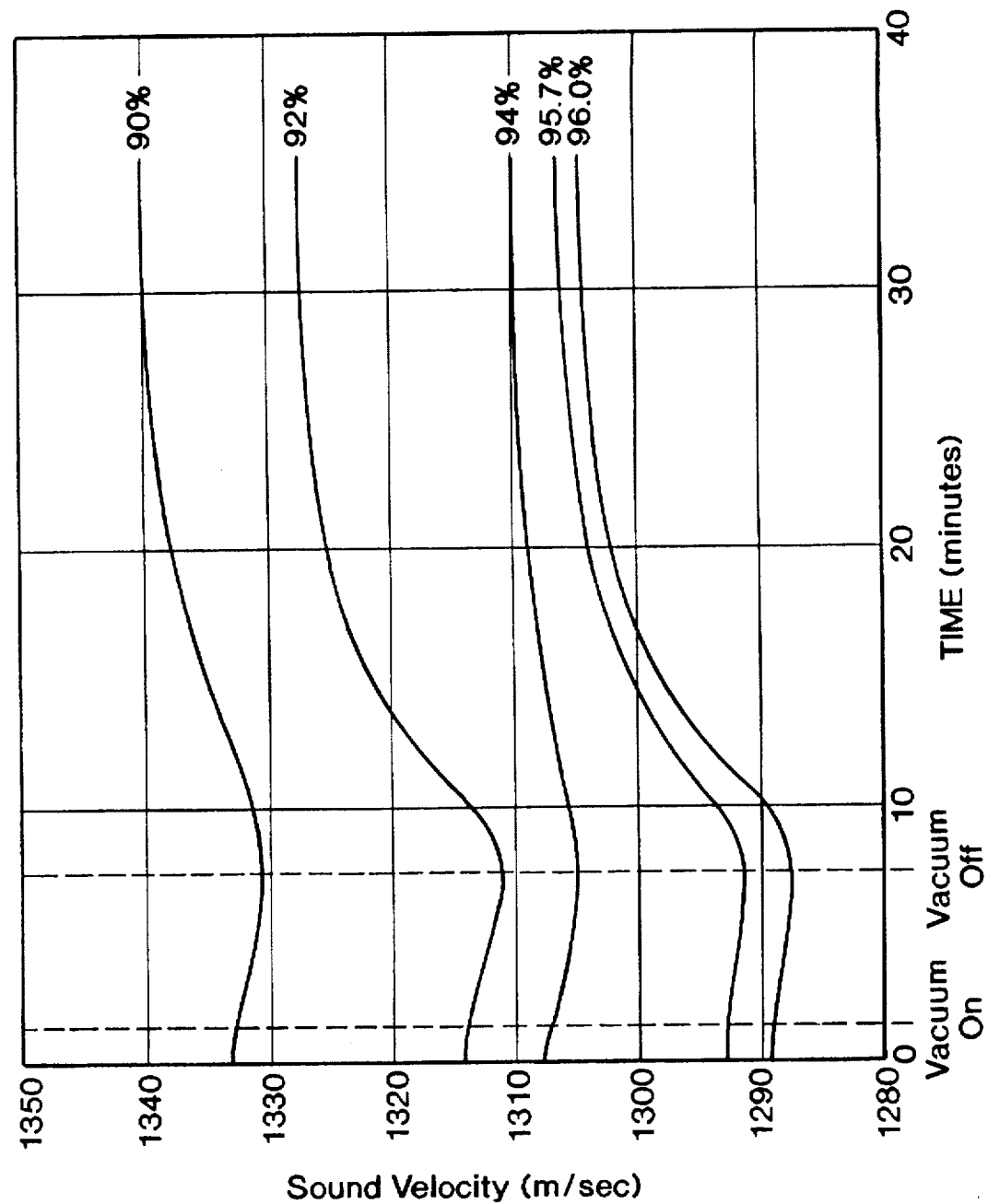
FIG. 4 is a graph showing the velocity of sound in the acid catalyst as a function of concentration and time as VOCs escape from the acid catalyst.

FIG. 4 is a graph showing typical normalized sound velocities over time as a function of acid concentration. The curves in FIG. 4 include a distinctive initial dip as vacuum is applied. The curves show that sound velocity gradually rises as time passes after the initial dip. Sound velocity is proportional to the square root of bulk modulus divided by density. Stratification gradually causes density and bulk modulus changes in the sample 21, specifically at the measured point between the sonic transducers 27 and 28, thereby changing the measured sound velocity. By locating the measurement point at the bottom of the cell 20 and using a measurement method that is essentially a point measurement with respect to vertical displacement in the cell 20, the resolution of the measurement is maximized. Placing the sonic transducers 27, 28 at a different vertical position on the cell 20 would result in a different curve shape. For example, placing the sonic transducers 27, 28 across the upper portion of the sample 21 would result in a decreasing sound velocity curve. Sound velocity measurements could also be made with the sonic transducers 27, 28 located across the lower portion of the cell 20 as the sample 21 drains from the cell 20. This would extend the curves shown in FIG. 4 further to the right. These curves should gradually decrease as the upper portions of the sample 21 pass between the sonic transducers 27, 28 as the cell 20 drains.

The processor 29 is also programmed to apply a predetermined function to a series of the normalized sound velocity measurements to calculate the acid concentration in the sample 21. In the preferred embodiment, this function has the following form:

$$\text{Concentration} = C_0 + C_1 V_{Final} + C_2 V_{Initial} + C_3 V_{Min}$$

with the coefficients ($C_0$ through $C_3$) being determined by linear regression against the initial sound velocity ($V_{Initial}$), minimum sound velocity ($V_{Min}$), and final sound velocity ($V_{Final}$) using the normalized sound velocity curves illustrated in FIG. 4. For example, linear regression using the data shown in FIG. 4 results in the following coefficients:

$$C_0 = 1657.083$$

$$C_1 = 2.25644$$

$$C_2 = 0.017772$$

$$C_3 = 0.000799$$

In the preferred embodiment, the processor 29 uses the sonic transducers 27, 28 to measure the initial sound velocity ($V_{Initial}$) shortly after the sample 21 is drawn into the cell 20. The processor 29 repeatedly measures the sound velocity during the period while the vacuum is on, and calculates the minimum sound velocity ($V_{Min}$) encountered during this period. A fixed time (e.g., 10 to 30 minutes) is allowed to elapse after the vacuum is turned off before the processor 29 measures the final sound velocity ($V_{Final}$). These sound velocities are normalized by the processor 29 to compensate for temperature variations and are used as input variables in the function discussed above.

It should be expressly understood that other equivalent statistical methodologies could be used in place of linear correlation. For example, coefficients can be determined by non-linear regression. The initial, final, and minimum sound velocities are used as the input variables in the preferred embodiment because empirical studies indicate that this is sufficient for highly accurate measurements of acid concentration. However, other alternatives exist to using these three sound velocity measurements. A regression could be performed using an extended time series of measurements, logarithmic fits, or a series of measurements could be integrated over time to provide an alternative input variable.

Other types of instruments can be employed to produce related measurements, particularly since sound velocity and density are related as previously mentioned. For example, a densitometer can be used to directly measure changes in the density of the sample over time. A viscometer would also provide an indirect measurement of density.

Returning to FIG. 1, it should be noted that the acid concentration monitors 31–34 can be used to adjust control valves 41, 42, 43, and 44 regulating the feed rate of acid into each of the contactors 10, 12, 14, and 16. The embodiment shown allows direct control of all four stages of the alkylation plant. Each monitor cell 31–34 adjusts its control valve to maintain a desired acid concentration set point for its stage of the alkylation plant. It should be understood that this configuration could be simplified by using a single acid concentration monitor cell to control only the last stage of the alkylation plant, or two monitors could be used to control the first and last stages, respectively. The acid concentration monitors 31–34 can also provide a visual display to allow a human operator to manually control the acid feed rate.

The above disclosure sets forth a number of embodiments of the present invention. Other arrangements or embodiments, not precisely set forth, could be practiced under the teachings of the present invention and as set forth in the following claims.

I claim:

1. A system for measuring acid concentration in an acid solution sample containing volatile organic compounds (VOCs), acid, water and hydrocarbons from an alkylation process and used to optimize control of said alkylation process, said system comprising:

a cell for holding said sample and allowing VOCs to escape from the sample without any initial stripping, heat treatment, or other pre-treatment;

Measurement means for repeatedly measuring a physical property indicative of the density of said sample over time as the sample stratifies and as VOCs escape from the sample; and a computer or micro-processor for receiving said measurements and applying a predetermined function to a series of said measurements to compute the acid concentration in the sample.

2. The system of claim 1 wherein said means for measuring a physical property of said sample comprises means for measuring the velocity of sound through said sample.

3. The system of claim 1 wherein said means for measuring a physical property of said sample comprises a densitometer.

4. The system of claim 1 wherein said means for measuring a physical property of said sample comprises a viscometer.

5. The system of claim 1 wherein the sample is allowed to stratify within said cell during said measurements.

6. The system of claim 1 further comprising a temperature sensor for measuring the temperature of the sample, and wherein said computer or micro processor normalizes said measurements to compensate for variations in temperature.

7. The system of claim 1 further comprising vacuum means connected to said cell for expediting dissipation of VOCs from said sample.

8. The system of claim 1 wherein said processor applies said function to the initial measurement, minimum measurement, and final measurement after a predetermined period of time for the sample.

9. The system of claim 1 wherein said function is determined by statistical regression using measurements taken from samples having known acid concentrations.

10. A method for measuring acid concentration in an acid solution sample containing volatile organic compounds (VOCs), acid, water and hydrocarbons from an alkylation process and used to optimize control of said alkylation process, said method comprising:

holding the sample in a cell without any initial stripping, heat treatment, or other pre-treatment;

Repeatedly measuring the velocity of sound through at least a portion of the sample over time as VOCs escape from the sample and the sample stratifies in said cell; and applying a predetermined function to a series of said normalized sound velocity measurements to compute the acid concentration in the sample.

11. The method of claim 10 wherein said function is determined by regression using sound velocity measurements taken from samples having known acid concentrations.

12. The method of claim 10 wherein said function is applied to the initial sound velocity measurement, the minimum sound velocity measurement, and a final sound velocity measurement after a predetermined period of time.

13. The method of claim 10 further comprising the step of applying a vacuum to the sample to expedite dissipation of VOCs.

14. The method of claim 10 further comprising the steps of:

measuring the temperature of the sample in said cell; and normalizing said sound velocity measurements to compensate for variations in sample temperature.

15. A system for measuring acid concentration in a sample from an alkylation process containing volatile organic compounds (VOCs), said system comprising:

a cell for holding said sample and allowing VOCs to escape from the sample;

sensor means for repeatedly measuring the velocity of sound through at least a portion the sample over time as VOCs escape from the sample;

means for storing the initial sound velocity measurement for the sample from said sensor means;

means for determining and storing the minimum sound velocity measurement for the sample from said sensor means during a predetermined period of time;

means for storing the final sound velocity measurement for the sample from said sensor means during said predetermined period of time; and computer or micro processor means for applying a predetermined function to said initial sound velocity measurement, said minimum sound velocity measurement, and said final sound velocity measurement to compute the acid concentration in the sample.

16. The system of claim 15 wherein the sample is allowed to stratify within said cell during said sound velocity measurements.

17. The system of claim 15 further comprising a temperature sensor for measuring the temperature of the sample, and wherein said processor means normalizes said sound velocity measurements to compensate for variations in temperature.

18. The system of claim 15 further comprising vacuum means connected to said cell for expediting dissipation of VOCs from said sample.

19. The system of claim 15 wherein said function is determined by regression using measurements taken from samples having known acid concentrations.

* * * * *